United States Patent [19]

Welch et al.

[11] Patent Number: 4,781,713

[45] Date of Patent: Nov. 1, 1988

[54] INCONTINENCE PAD FOR FEMALES

[75] Inventors: Kathleen Welch, Cranston, R.I.; Terese Campion, Springfield, Mass.

[73] Assignee: Sherwood Medical Company, St. Louis, Mo.

[21] Appl. No.: 61,182

[22] Filed: Jun. 10, 1987

[51] Int. Cl.$^4$ .............................................. A61F 13/16
[52] U.S. Cl. .............................. 604/385.1; 604/378; 604/387
[58] Field of Search ............... 604/378, 381, 386, 387, 604/389, 390, 391, 392

[56] References Cited

U.S. PATENT DOCUMENTS

| | | |
|---|---|---|
| 3,741,212 | 6/1973 | Schutte . |
| 4,046,147 | 9/1977 | Berg . |
| 4,327,732 | 5/1982 | Thinnes . |
| 4,333,462 | 6/1982 | Holtman et al. . |
| 4,501,586 | 2/1985 | Holtman . |
| 4,560,379 | 12/1985 | Stemmier . |
| 4,578,066 | 3/1986 | O'Connor . |
| 4,592,751 | 6/1986 | Gegelys . |
| 4,595,392 | 6/1986 | Johnson et al. . |
| 4,710,187 | 12/1987 | Boland et al. ................ 604/385 X |
| 4,731,065 | 3/1988 | Yamada ....................... 604/378 X |

*Primary Examiner*—Allen M. Ostrager
*Attorney, Agent, or Firm*—Brumbaugh, Graves, Donohue & Raymond

[57] ABSTRACT

A disposable incontinence pad to be worn by a female. The pad is an essentially two part design including a moisture multi-layered absorbent pad encase in a moisture resistant hydrophobic layer which prevents leakage of urine to the skin of the wearer. The pad has an essentially ovoid opening on the side facing the wearer. Securely attached to the opening into the pad is an essentially ovoid, resilient contoured rim portion which surrounds and conforms itself to the vulvar region of the wearer. The rim portion is contoured so as to direct urine flow into the absorbent pad with minimal splashback while at the same time preventing urine from contacting the user.

9 Claims, 2 Drawing Sheets

INCONTINENCE PAD FOR FEMALES

BACKGROUND OF THE INVENTION

The present invention relates to an improved incontinence pad for use by females. More specifically, the incontinence pad is an improved two part design: a highly absorbent pad plus a contoured rim structure attached thereto. The rim portion is designed to encompass the entire vulvar region.

Absorbent materials, e.g., pads and undergarments are frequently used for treating urinary incontinence in females. The use of such garments, however, is generally unsuitable for extended periods of time. Absorbent pads are bulky, uncomfortable and non-hygenic. In addition, the pads which are currently available often leak to the back or sides and promote the spread of odor and skin irritation due to urine being in direct contact with the skin of the user. Furthermore, the pads must be changed frequently since urine trapped within is an excellent medium for the growth of bacteria and other microorganisms which can cause not only severe irritation but infection of sensitive skin which is in contact with the pad. There is also a significant risk of serious internal infection in users of currently available pads, particularly those users who are bedridden.

These problems are substantially eliminated by the present invention which provides for a highly absorbent pad in combination with a contoured rim portion which contacts the wearer.

SUMMARY OF THE INVENTION

Accordingly, it is a principal object of the present invention to provide for use by a female an improved incontinence garment which combines a specifically designed highly moisture-absorbent multi-layered pad with a contoured rim portion attached to the pad. Thus, the incontinence pad of the present invention is a two part configuration composed of a highly moisture-absorbent pad encased in a moisture-resistant hydrophobic layer, which in turn is surrounded by a hydrophilic layer; the pad having securely attached thereto on a surface of the pad contacting the user a resilient contoured rim portion which surrounds and conforms itself to contact the entire vulvar region of the user. The rim portion is contoured so as to direct urine flow into the absorbent pad with minimal splash back, while at the same time preventing urine from contacting the sensitive vulvar tissue.

In accordance with the present invention, the rim portion is comfortable to the wearer and suitable for a wide range of differently sized women. The contoured rim portion prevents back flux of urine to the pad from the back side of the rim. To accomplish the above objectives, the rim portion is made from a polyurethane foam, made hydrophobic, or from a non-woven material, such as polyester which promotes urine flow into the absorbent pad.

Also according to the invention, the absorbent pad to which the rim portion is attached is specifically designed to accomodate the flow of urine at high rates. Accordingly, the pad is formed from several layers: a central layer made of a superabsorbent material which is sandwiched between two highly absorbent layers made from an absorbent material such as cellulose fluff or synthetic fluff material. The absorbent materials for constructing the pad are chosen to accomodate a urine flow rate up to 25 cc/second. The layers of the absorbent pad can absorb up to 300 cc of urine.

In addition to the foregoing object of providing a highly absorbent pad designed so that urine flow is directed into the pad, it is a further object of the present invention to provide a pad which is essentially a closed system thereby retaining odor. Furthermore, the incontinence pad minimizes leakage to undergarments, while at the same time, prevents urine from contacting the skin of the user. Accordingly, the absorbent layers of the pad are encased in a hydrophobic layer, such as a polypropylene or polyethylene film, which prevents urine from contacting the skin, minimizes leakage, and retains odor. A hydrophilic layer, such as non-woven polyester, which surrounds the absorbent pad and hydrophobic layer, serves as a comfortable facing fabric for contact with the skin of the user, as well as an absorbent to pick up any residual drops of urine which may escape from the rim portion.

Other objects, features and advantages of the present invention will be apparent by reference to the following description of preferred embodiments, drawings and claims.

BRIEF DESCRIPTION OF THE DRAWINGS

The invention may be better understood from the following detailed description, taken in conjunction with the accompanying drawing in which.

DESCRIPTION OF THE PREFERRED EMBODIMENTS

Figure 1:
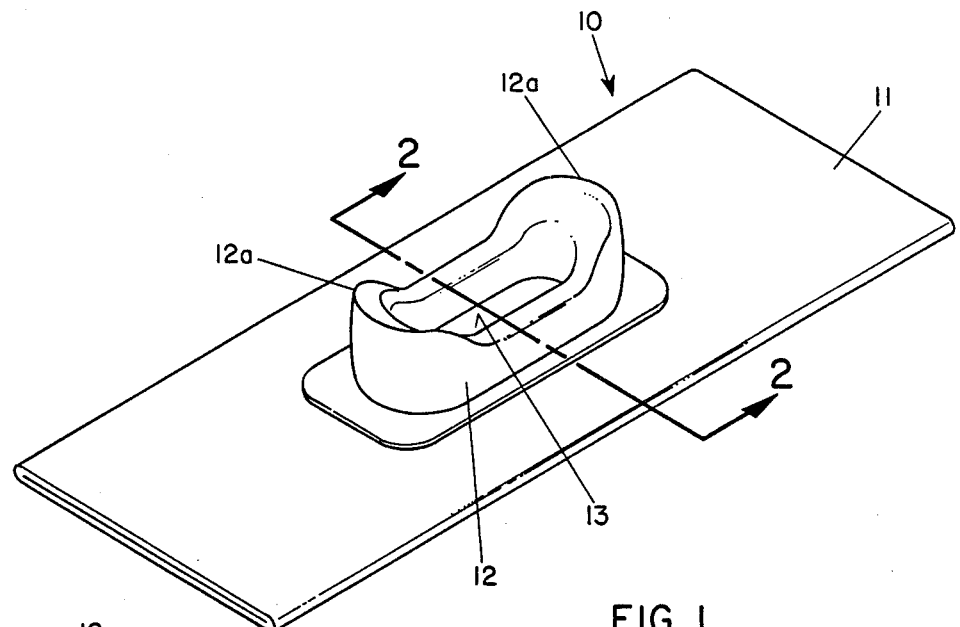
FIG. 1 is a perspective view of an incontinence pad according to one embodiment of the invention.

In accordance with one preferred embodiment of the present invention which is designed to be worn like a diaper in a generally neutral/dorsal orientation, the incontinence pad 10 shown in FIG. 1 is a rectangular-shaped diaper-like absorbent pad 11 having on one side and securely attached thereto an essentially ovoid contoured resilient rim portion 12. The rim portion 12, which is formed preferably from a polyurethane foam or non-woven polyester, that has been treated to render it hydrophobic is sized to surround inter alia the entire vulvar region of various sized females.

The rim portion 12 has an essentially ovoid opening 13 therein through which urine can flow into pad 11. When in use, rim portion 12 fits over and surround the vulvar region in a generally neutral/dorsal orientation. Accordingly, the ends 12a of rim portion 12 are tapered and upwardly curved to allow for a snug but comfortable fit and to direct urine flow into the pad.

Figure 2:
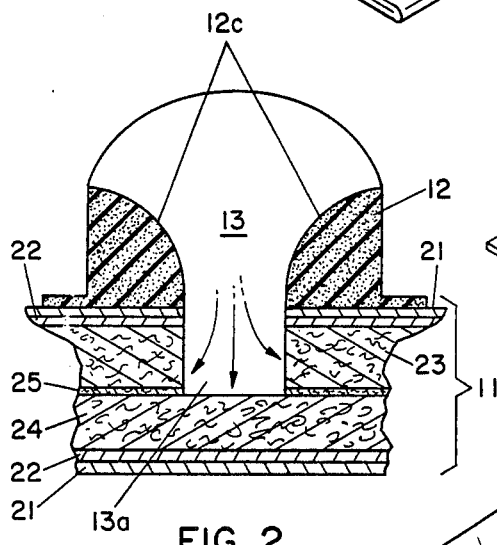
FIG. 2 is a cross-section through line 2—2 of FIG. 1.

With reference to FIG. 2 which is a cross-section through line 2—2 of the pad and rim portion shown in FIG. 1, it is seen that pad 11 is composed of multiple layers. The pad is fabricated to accomodate a urine flow of at least 25 cc per second. Up to 300 cc of urine can be absorbed by the pad without any leakage or odor. Layer 21 comprises a sheet of nonwoven absorbent material, preferably polyester, which surrounds and covers pad 11 and is the portion of the pad in contact with the user. Layer 22, which is immediately adjacent and internal to layer 21, is a hydrophobic layer, designed to prevent urine leakage from pad 11. Preferred materials for layer 22 include films made of polypropylene or polyethylene. Layers 23 and 24 are absorbent layers which absorb the urine flow. Particularly preferred materials for fabricating layers 23 and 24 include cellulose fluff or a synthetic fluff. Layer 25, which is sandwiched between layers 23 and 24, is a superabsorbent layer.

The contoured inner walls 12c of rim portion 12 which face opening 13 are also readily apparent in FIG. 2. The inner walls 12c are designed so as to direct urine flow into the pad. Opening 13 is in direct communication with opening 13a in pad 11 which allows urine flow to be directed to the absorbent layers 23 and 24 and superabsorbent layer 25.

Figure 3:
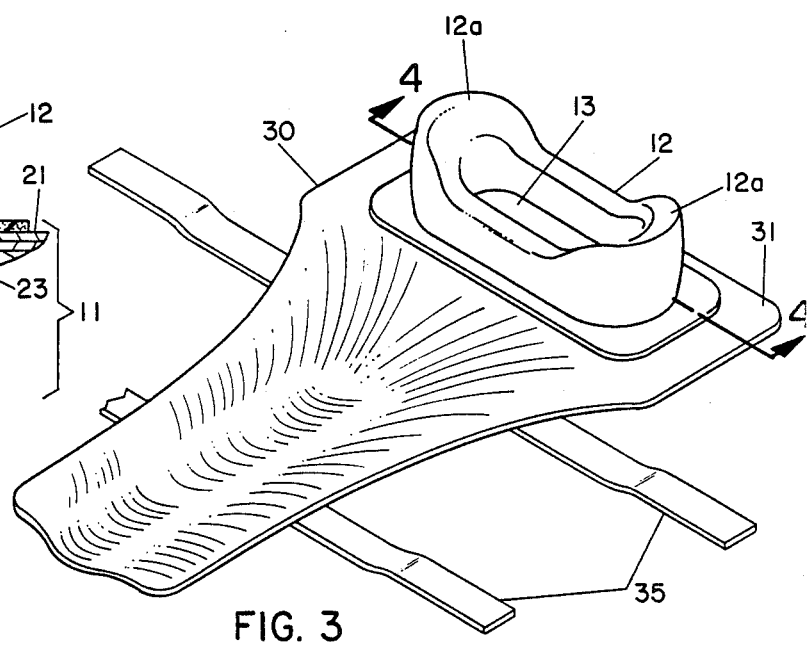
FIG. 3 is a perspective view of an incontinence pad according to a second embodiment of the invention.
Figure 4:
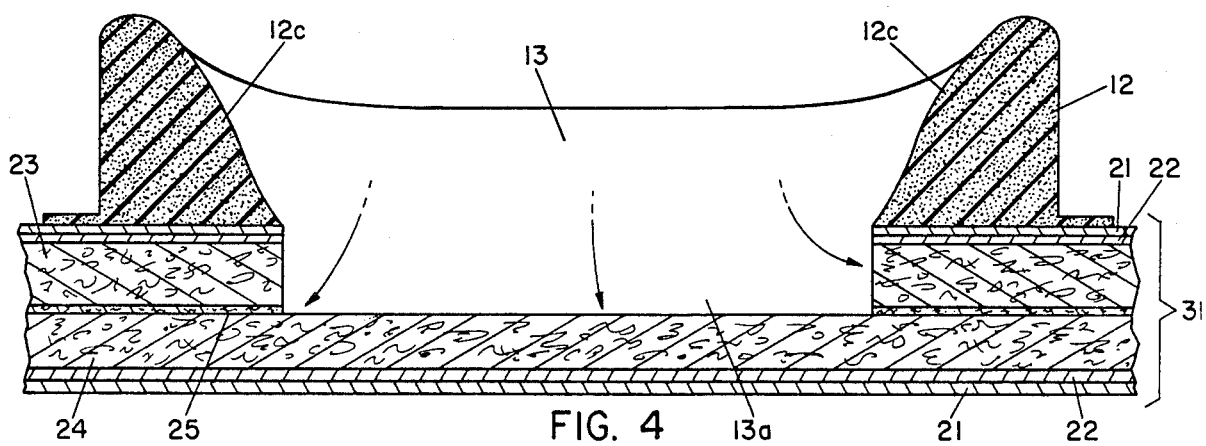
FIG. 4 is a cross-section through line 4—4 of FIG. 3.
Figure 5:
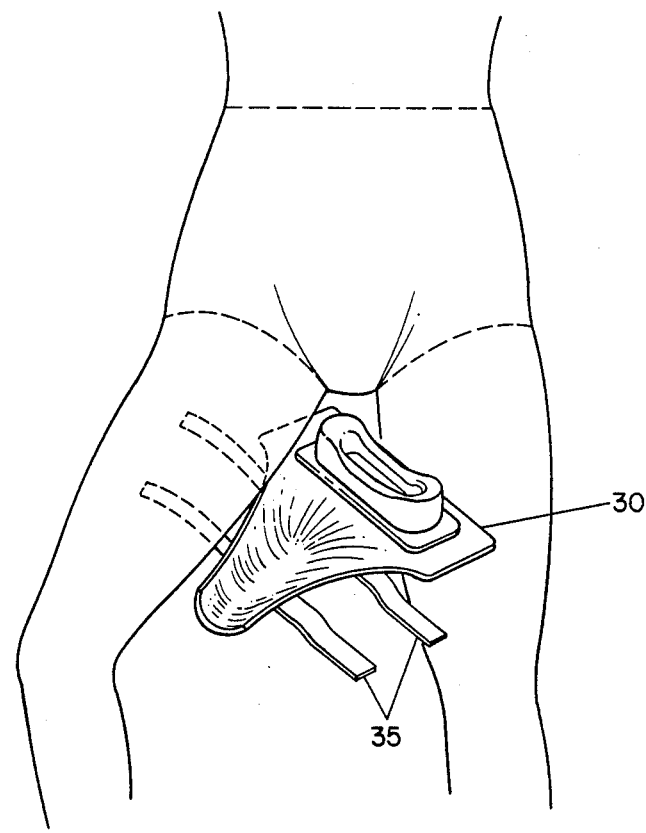
FIG. 5 is a perspective view of the embodiment of FIG. 3 in use by a patient.

FIG. 3 depicts a second embodiment of the incontinence pad 30 of the invention. Pad 31 has a bag-like shape with rim 12 affixed to an upper portion thereof. Opening 13 is in communication with the inner absorbent layers of pad 31, which are shown in FIG. 4. Rim portion 12 is meant to be worn in an essentially ventral/dorsal direction as can be seen from the upwardly curved tapered ends 12a of rim portion 12. Also apparent in FIG. 3 are leg straps 35 which are used to affix the incontinence garment 30 to the wearer's leg. Leg straps 35 can be fabricated from an adhesive material. Alternatively, they can have a material such as Velcro at the end to provide a means for securing the garment to the user. FIG. 5 depicts the incontinence pad of FIG. 3 in use.

Figure 6:
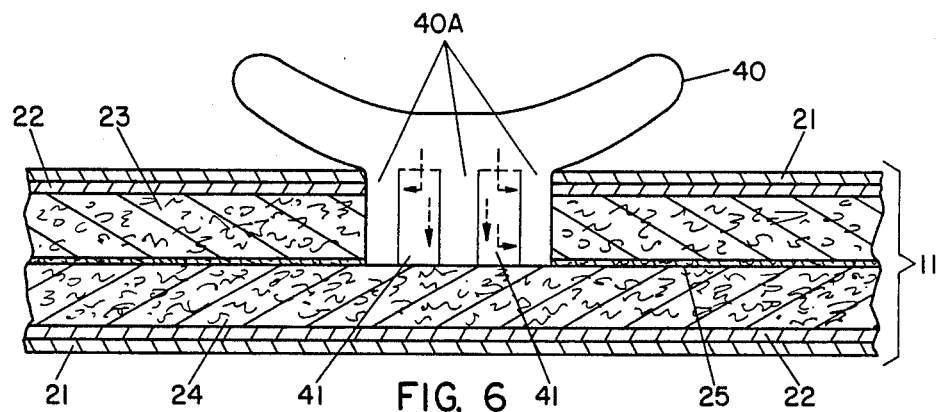
FIG. 6 is a partial cross-sectional view through the rim and pad of a further embodiment of the invention.

An alternate embodiment of the rim portion of the incontinence pad according to the present invention is shown in FIG. 6. Rim portion 40, like rim portion 12, is tapered and upwardly curved to fit the female vulvar region. Several projections 40a of the rim portion which extend into pad 11 and are in contact with super absorbent layer 25, define several openings 41 through which urine can flow into the pad.

Figure 7:
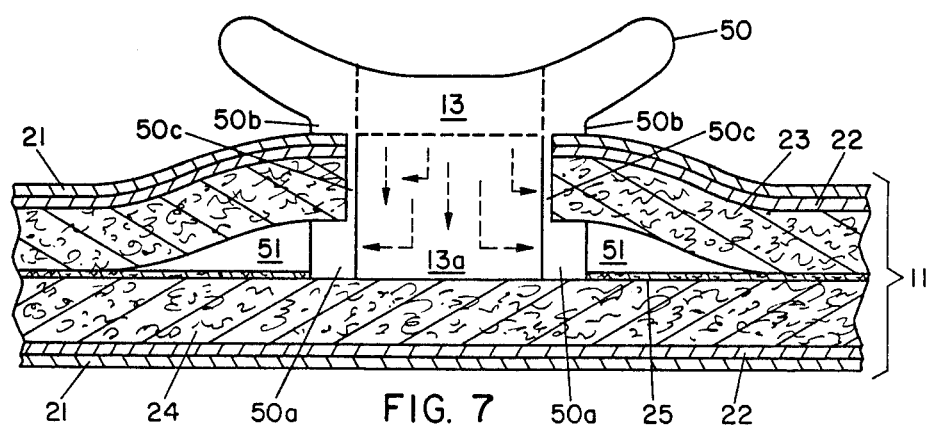
FIG. 7 is a partial cross-sectional view through the rim and pad of a still further embodiment of the invention.

FIG. 7, shows a still further embodiment of the rim portion. The upper part of the rim portion 50, which is upwardly curved to fit securely over the vulvar region, has projections 50c which extend into the pad and define and surround openings 13 of the rim portion and 13a of the pad. Rim projection 50c ends in a perpendicularly oriented projection 50a which extends into the pad between absorbent layer 23 and superabsorbent layer 25. The projection of part 50a into the pad provides an air space 51 between layers 23 and 25. At the upper portion of rim 50, on a lower portion thereof, part 50b is extended to be in contact with absorbent layer 21 and hydrophobic layer 22 on the upper face of pad 11 and is designed to further prevent urine leakage to the outside of the pad. Rim portion 50 and projections 50c and 50a serve to efficiently direct urine flow into the internal portion of page 11.

The foregoing embodiments of the female incontinence pad according to the invention are merely illustrative of those currently preferred. Modifications of the garment and techniques in its manufacture will be obvious to those skilled in the art and hence, what is specifically disclosed is not intended in any way to limit the scope of the invention claimed hereinbelow.

We claim:

1. A disposable incontinence pad to be worn by a female comprising a highly moisture-absorbent multi-layered pad encased in a moisture-resistant hydrophobic layer which in turn is surrounded by a moisture absorbent-hydrophilic layer, said pad having an essentially ovoid opening therein and having securely attached thereto on a surface of the pad contacting a user an essentially ovoid resilient contoured rim portion defining an essentially ovoid opening which is continuous with said opening in said pad, said rim portion surrounding and conforming itself to the entire vulvar region of the user and surrounding and being in contact with said opening in said pad, the rim portion being contoured so as to direct urine flow into the absorbent pad with minimal splash-back while at the same time preventing urine from contacting the vulvar tissue.

2. Incontinence pad as in claim 1 in which the rim is made from polyurethane foam or polyester.

3. Incontinence pad as in claim 2 in which the polyurethane foam rim portion is made hydrophobic so as to promote urine flow into the absorbent pad.

4. Incontinence pad as in claim 1 wherein the moisture absorbent pad comprises a central layer of superabsorbent material surrounded by two outside layers of absorbent material.

5. Incontinence pad as in claim 4 in which the absorbent material is selected from the group consisting of cellulose fluff and synthetic fluff material.

6. Incontinence pad as in claim 4 in which the pad accomodates a urine flow into the pad at a flow rate of up to 25 cc per second.

7. Incontinence pad as in claim 4 in which the layers of the pad can absorb up to 300 cc of urine.

8. Incontinence pad as in claim 1 in which the hydrophobic layer is a film selected from the group consisting of polyethylene and polypropylene.

9. Incontinence pad as in claim 1 in which the hydrophilic layer is a cover sheet formed from nonwoven absorbent polyester.

* * * * *